(12) United States Patent
Garrison et al.

(10) Patent No.: US 11,871,951 B2
(45) Date of Patent: Jan. 16, 2024

(54) SURGICAL TOOL SEAL

(71) Applicant: ARTHREX, INC., Naples, FL (US)

(72) Inventors: Troy Garrison, Fort Myers, FL (US);
Chris Godfrey, Fort Myers, FL (US)

(73) Assignee: ARTHREX, INC., Naples, FL (US)

( * ) Notice: Subject to any disclaimer, the term of this patent is extended or adjusted under 35 U.S.C. 154(b) by 267 days.

(21) Appl. No.: 17/359,201

(22) Filed: Jun. 25, 2021

(65) Prior Publication Data
US 2022/0409231 A1 Dec. 29, 2022

(51) Int. Cl.
*A61B 17/32* (2006.01)
*A61B 17/34* (2006.01)
*A61B 17/00* (2006.01)

(52) U.S. Cl.
CPC .. *A61B 17/320016* (2013.01); *A61B 17/3417* (2013.01); *A61B 2017/00477* (2013.01); *A61B 2017/3419* (2013.01); *A61B 2562/226* (2013.01)

(58) Field of Classification Search
CPC ...... A61B 17/32002; A61B 17/320016; A61B 17/320783; A61B 17/3417; A61B 2017/00477; A61B 2017/2948; A61B 2017/320024; A61B 2017/3419; A61B 2562/226
See application file for complete search history.

(56) References Cited

U.S. PATENT DOCUMENTS

| | | | |
|---|---|---|---|
| 8,535,342 B2 | 9/2013 | Malackowski et al. | |
| 9,186,166 B2 | 11/2015 | Thistle | |
| 9,345,504 B2 | 5/2016 | McCombs | |
| 10,736,642 B2 | 8/2020 | Burke | |
| 2008/0021487 A1* | 1/2008 | Heisler | A61B 17/32002 606/170 |
| 2008/0132928 A1* | 6/2008 | Jezierski | A61B 17/32002 606/167 |
| 2008/0188848 A1* | 8/2008 | Deutmeyer | A61B 18/1485 606/45 |
| 2016/0030057 A1* | 2/2016 | Loreth | A61B 17/1628 606/167 |
| 2019/0038305 A1* | 2/2019 | Smith | A61B 90/39 |
| 2020/0297373 A1 | 9/2020 | Staunton et al. | |

* cited by examiner

*Primary Examiner* — Jocelin C Tanner
(74) *Attorney, Agent, or Firm* — KARISH & BJORGUM, PC

(57) ABSTRACT

A surgical tool having an inner drive hub coupled to an inner shaft, the inner drive hub having a boss; an outer hub coupled to a hollow outer shaft, the outer drive hub having at least one hole; and a seal having a body and at least one tab; wherein the inner drive hub and the inner shaft are configured for insertion inside the outer hub and the hollow outer shaft such that the boss is positioned distally to the at least one hole; and the seal body is positioned outside of the outer hub and the at least one tab extends through the at least one hole and proximally to the boss to removably couple the inner drive hub and the inner shaft to the outer hub and the hollow outer shaft.

19 Claims, 5 Drawing Sheets

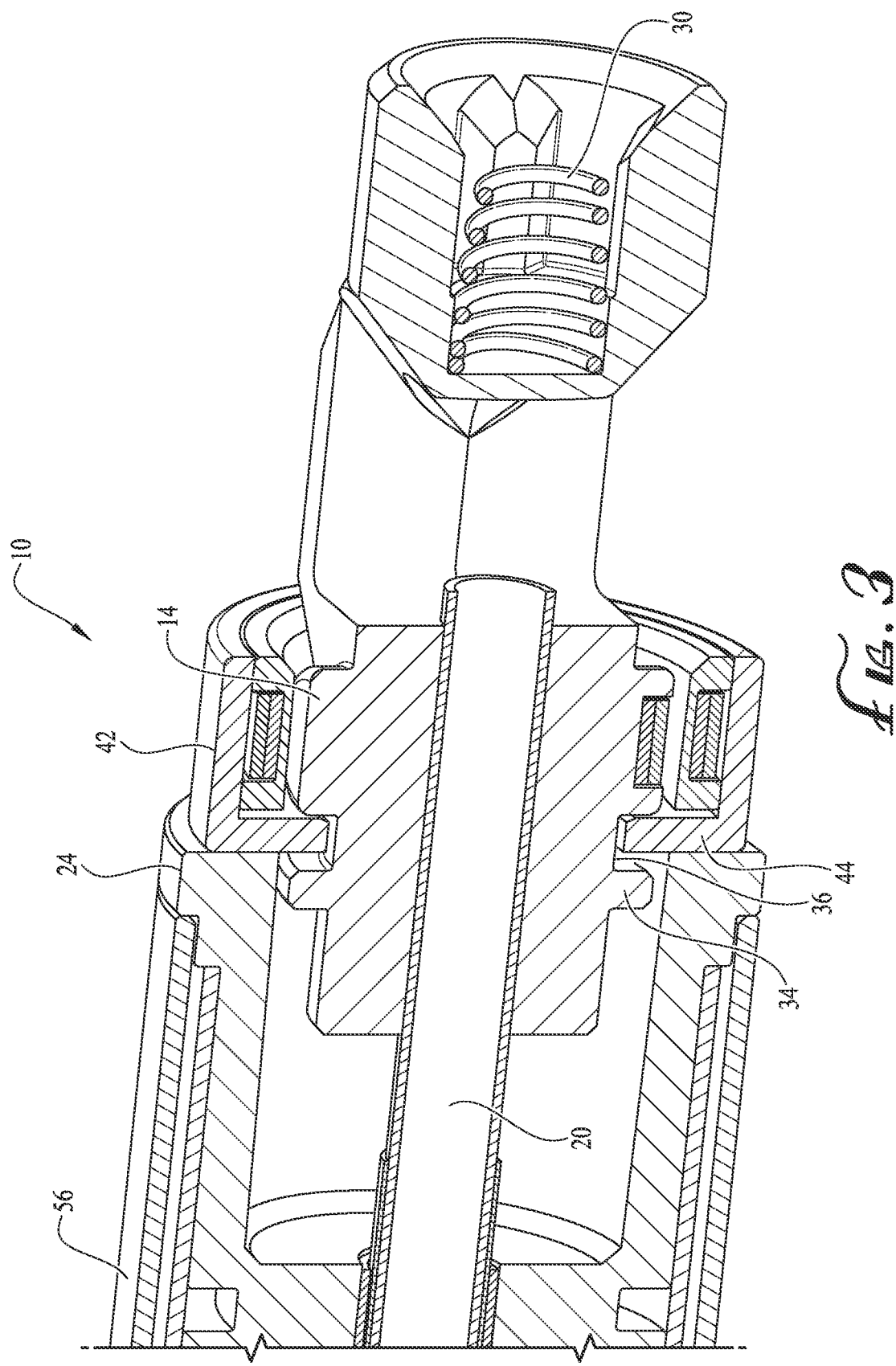

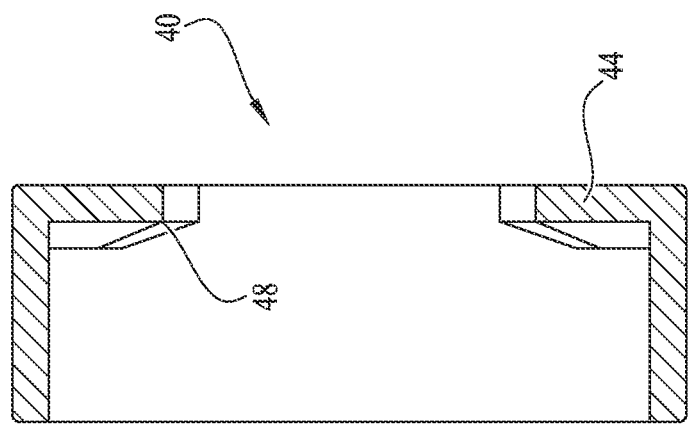
_Fig. 5_
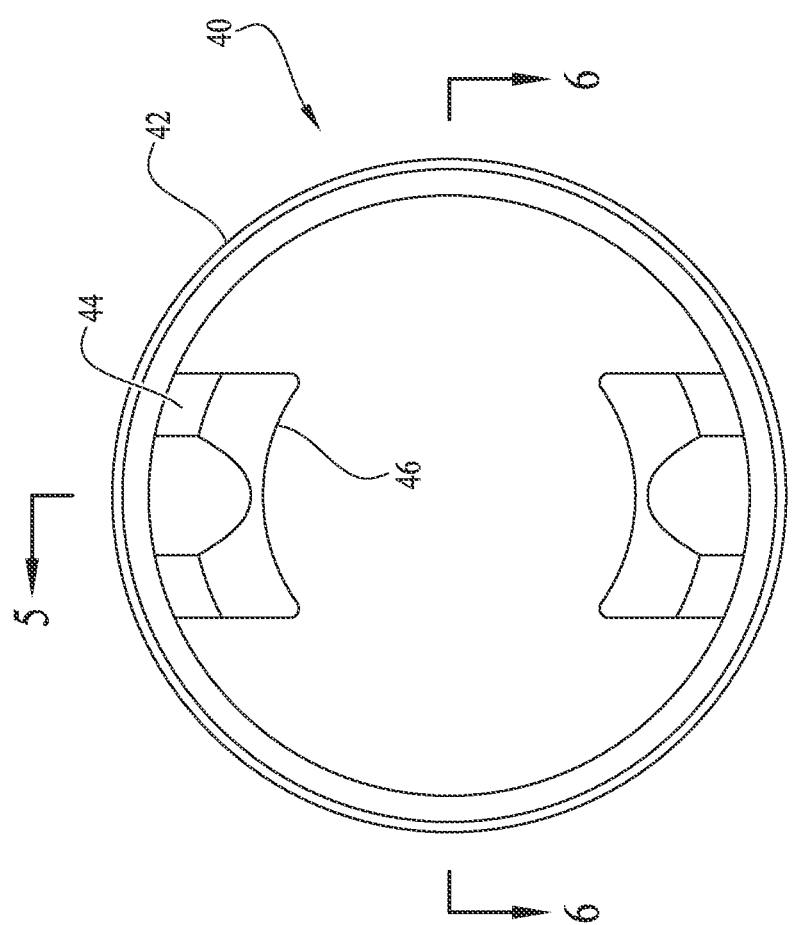
_Fig. 4_

SURGICAL TOOL SEAL

BACKGROUND

The present disclosure relates to devices used in endoscopic surgery and, more particularly, to a surgical tool having a seal for holding the tool together.

Certain surgical tools, such as shavers, typically have an inner shaft that rotates relative to an outer shaft. The surgical tool is connectable to a handpiece where a motor rotates the inner shaft. However, when the surgical tool is not connected to a handpiece the components of the surgical tool may become detached. If the components of the surgical tool become detached then the surgical tool may be damaged. Additionally, the loose components of the surgical tool, some of which may have sharp edges, may pose a risk of injury to patents and healthcare providers.

Accordingly, there exists a need for a system and method of holding the components of a surgical tool together that remedies the shortcomings of the prior art.

SUMMARY

According to implementations, the present disclosure is directed to a surgical tool having an inner drive hub coupled to an outer drive hub using a seal.

In an implementation, the surgical tool has: an inner drive hub coupled to an inner shaft, the inner drive hub having a boss; an outer hub coupled to a hollow outer shaft, the outer drive hub having at least one hole; and a seal having a body and at least one tab. The inner drive hub and the inner shaft are configured for insertion inside the outer hub and the hollow outer shaft such that the boss is positioned distally to the at least one hole. The seal body is positioned outside of the outer hub and the at least one tab extends through the at least one hole and proximally to the boss to removably couple the inner drive hub and the inner shaft to the outer hub and the hollow outer shaft.

The at least one hole may be configured as a slot. The at least one tab may have a chamfered edge. The at least one tab may have a barb. In an implementation, the outer hub has a plurality of holes and the seal has a plurality of tabs; and the seal is configured such that each of the plurality of tabs is inserted into a different one of the plurality of holes. Each tab may have a rounded inner portion configured with a radius slightly larger than the radius of the inner drive hub.

In an implementation, the seal is made of silicon rubber. The inner shaft may be hollow and configured for connection to a drive hub with a suction device. A first magnet may be coupled to the inner drive hub and a second magnet coupled to the outer hub. An RFID tag may be coupled to the outer hub. An RFID cover may be coupled to the outer hub over the RFID tag. A blade may be coupled to a distal end of the inner shaft and a cutting head coupled to a distal end of the outer shaft.

In an implementation, the at least one tab cooperates with the inner drive hub boss to prevent the inner drive hub from being removed from the outer hub without removing the seal from the assembly. If the inner drive hub is pulled outward from the outer hub, the boss may force the at least one tab to bend and become wedged between the boss and the outer hub, thereby preventing the boss from moving past the tab and preventing the inner drive hub from being withdrawn from outer hub.

In an implementation, a surgical cutting tool has: an inner drive hub coupled to an inner shaft, the inner drive hub having a groove; an outer hub coupled to a hollow outer shaft, the outer drive hub having a plurality of slots; and a seal having a body and a plurality of tabs extending substantially perpendicularly from the body. The inner drive hub and the inner shaft are configured for insertion inside the outer hub and the hollow outer shaft such that the groove is positioned proximally to the plurality of slots; the seal body is positioned outside of the outer hub; and each of the plurality of tabs extends through a separate one of the plurality of slots and into the groove to removably couple the inner drive hub and the inner shaft to the outer hub and the hollow outer shaft.

The plurality of slots may be positioned on opposite sides of the outer hub. The plurality of tabs may each have a rounded inner portion configured with a radius slightly larger than the radius of the groove. Each of the tabs may have a chamfered edge. The seal may be made of silicon rubber.

In an implementation, the tabs cooperate with the inner drive hub boss to prevent the inner drive hub from being removed from the outer hub without removing the seal from the assembly. If the inner drive hub is pulled outward from the outer hub, the boss may force the tabs to bend and become wedged between the boss and the outer hub, thereby preventing the boss from moving past the tab and preventing the inner drive hub from being withdrawn from outer hub.

According to an implementation, the present disclosure is also directed to a method of making a surgical tool, wherein the surgical cutting tool comprises an inner drive hub coupled to an inner shaft, the inner drive hub further comprising a boss; an outer hub coupled to a hollow outer shaft, the outer drive hub further comprising at least one hole; and a seal comprising a body and at least one tab, the method comprising the steps of: inserting the inner drive hub and inner shaft into the outer hub and the outer shaft until the boss is positioned distal to the at least one hole; placing the seal over the outer hub; and inserting the at least one tab through the at least one hole until the at least one tab extends inside of the outer hub and proximal to the boss.

These and other features are described below.

BRIEF DESCRIPTION OF THE DRAWINGS

The features, aspects and advantages of the present invention will become better understood with regard to the following description, appended claims and accompanying figures wherein:

FIG. 3 is a cut-away side elevation perspective view of a portion of a surgical tool according to an implementation;

FIG. 4 is a top elevation view of a seal usable in the surgical tool of FIG. 1;

FIG. 5 is a cut away view of the seal of FIG. 4 taken along line 5-5;

DETAILED DESCRIPTION

In the following description of the preferred implementations, reference is made to the accompanying drawings which show by way of illustration specific implementations in which the invention may be practiced. Wherever possible, the same reference numbers will be used throughout the drawings to refer to the same or like parts. It is to be understood that other implementations may be utilized and structural and functional changes may be made without departing from the scope of this disclosure.

Figure 1:
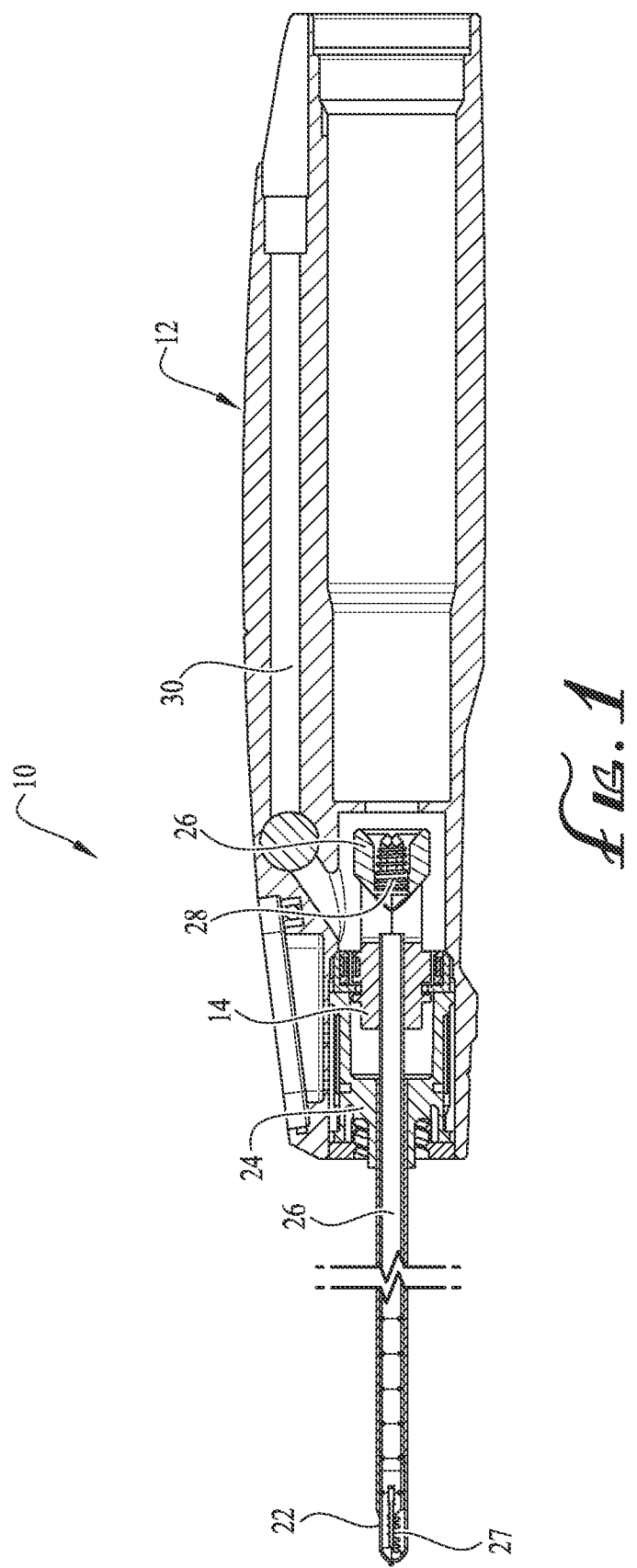
FIG. 1 is partially cut-away side elevation view showing a surgical tool coupled to a handpiece according to an implementation.

FIG. 1 shows a surgical tool 10 according to an implementation coupled to a handpiece 12. The illustrated surgical tool 10 is a shaver. However, a seal as taught herein may be used in many additional types of surgical tools having an inner shaft and an outer shaft, such as, without limitation, drills, burrs, and rasps.

With reference to FIGS. 1 to 7, a surgical tool 10 according to an implementation has an inner drive hub 14. The inner drive hub 14 has a proximal end 16 and a distal end 18. An inner shaft 20 is coupled to the distal end 18 of the inner drive hub 14. A blade 22 or other implement may be coupled to a distal end of the inner shaft 20. The inner drive hub 14 may be made from plastic and molded around the inner shaft 20 which may be made from metal.

The surgical tool 10 also has an outer hub 24 and an outer shaft 26 coupled to the outer hub. A cutting head 27 or other surgical implement may be coupled to a distal end of the outer shaft 26. The outer shaft 26 is hollow. In an implementation, the inner shaft 20 is also hollow. The outer shaft 26 length may be varied depending on the desired application. In an implementation, the outer shaft 26 has a length of between about 50 mm and about 150 mm.

The inner drive hub 14 is connectable to a drive head 28 in the handpiece 12. In an implementation a spring 30, such as without limitation a conical spring, is coupled to the inner drive hub 14 and is configured to interface between the drive head 28 and the proximal end 16 of the inner drive hub. The handpiece 12 may have a suction pathway 32 for connection to a suction source (not shown). The suction pathway 30 may extend through the handpiece 12 and be in fluid communication with the inner drive hub 14 and the inner shaft 20. Suction may assist in pulling fluid and tissue into the blade 22 and cutting head 27 or other implements positioned at the distal ends of the inner shaft 20 and the outer shaft 26. In an additional implementation, liquid or pressurized gas may be communicated into the suction pathway 30 and out through the blade 22 and cutting head 27 or other implements.

Figure 2:
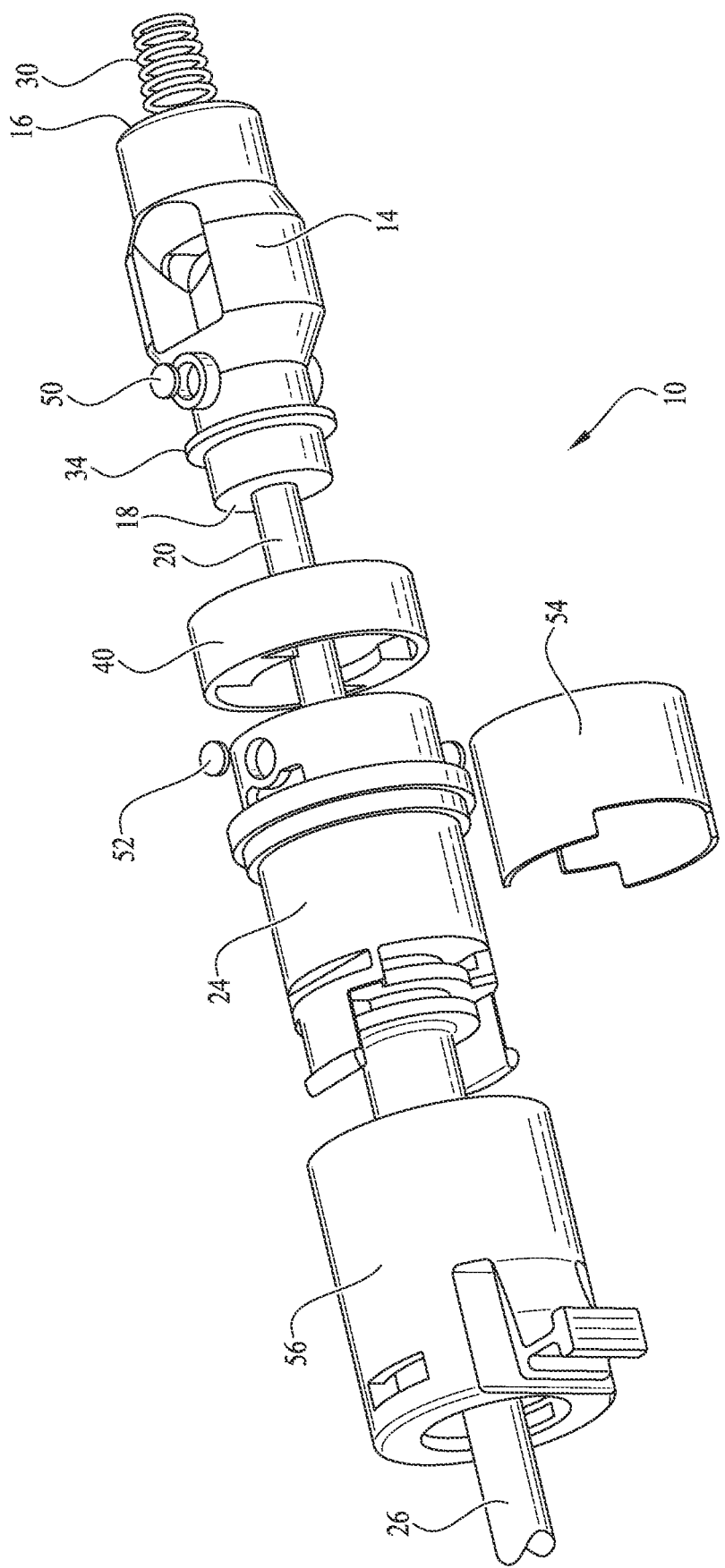
FIG. 2 is an exploded perspective view of a surgical tool according to an implementation.

As shown in FIGS. 2 and 3, the inner drive hub 14 has a boss 34. In an implementation, the boss 34 extends circumferentially around an outside of the inner drive hub 14. In an implementation, the boss 34 is configured in combination with rest of the inner drive hub 14 to form a circumferential groove 36 around an outer surface of the inner drive. In an implementation, the boss is from about 0.04 inch to about 0.06 inch larger than the diameter of the inner drive hub 14. In an implementation, the gap between the boss 34 and the wall of the outer hub 24 is between about 0.01 inch and about 0.03 inch.

The outer hub 24 has at least one hole 38. In an implementation, the outer hub 24 has a plurality of holes 38 positioned around an outer circumference of the outer hub 25. The holes 38 may have a variety of shapes and may be shaped as slots. When the inner shaft 20 is positioned in the outer shaft 26 and the inner drive hub 14 is positioned inside the outer hub 24, the boss 34 is positioned distal to the holes 38. A seal 40 couples the inner drive hub 14 to the outer hub 24.

Figure 6:
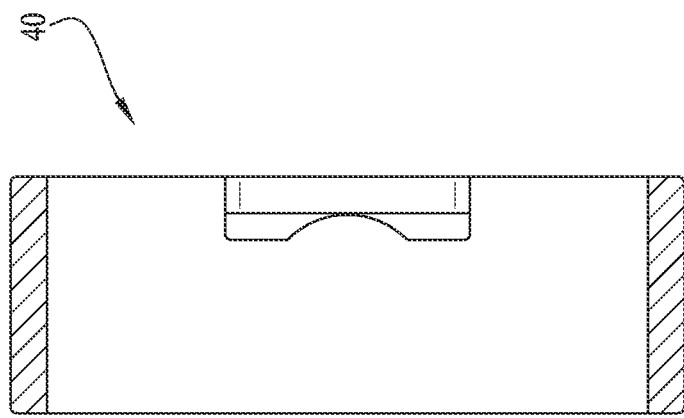
FIG. 6 is a cut away view of the seal of FIG. 4 taken along line 6-6.

As shown in FIGS. 4 to 6, the seal 40 has a body 42 and at least one tab 44. In an implementation, the seal 40 has a plurality of tabs 44 extending at an angle from the body. In an implementation, the tabs 44 extend inward substantially perpendicularly from the body. In an implementation, the body 42 is cylindrical and has an inner diameter configured to fit around an outside of the outer hub. The tabs 44 are configured to fit through the outer hub holes 38 and be positioned proximal to the boss 34. Once the tabs 44 are positioned proximal to the boss, the inner drive hub cannot be removed from a proximal end of the outer hub because of interference between the boss 34 and the tabs 44.

The tabs 44 have an interior portion 46 configured extend below the height of the boss without contacting the boss or the inner drive hub 14 as the inner drive hub is rotated. The interior portion 46 may rounded. The interior portion 46 may be rounded with a radius slightly larger than a radius of the inner drive hub groove 36. In an implementation, the interior surface 46 has a radius of from about 0.17 inch to about 0.18 inch. In an implementation, the tabs 44 have a length of from about 0.1 inch to about 0.125 inch, a thickness of from about 0.05 inch to about 0.07 inch and a width of from about 0.23 inch and about 0.25 inch.

Figure 7:
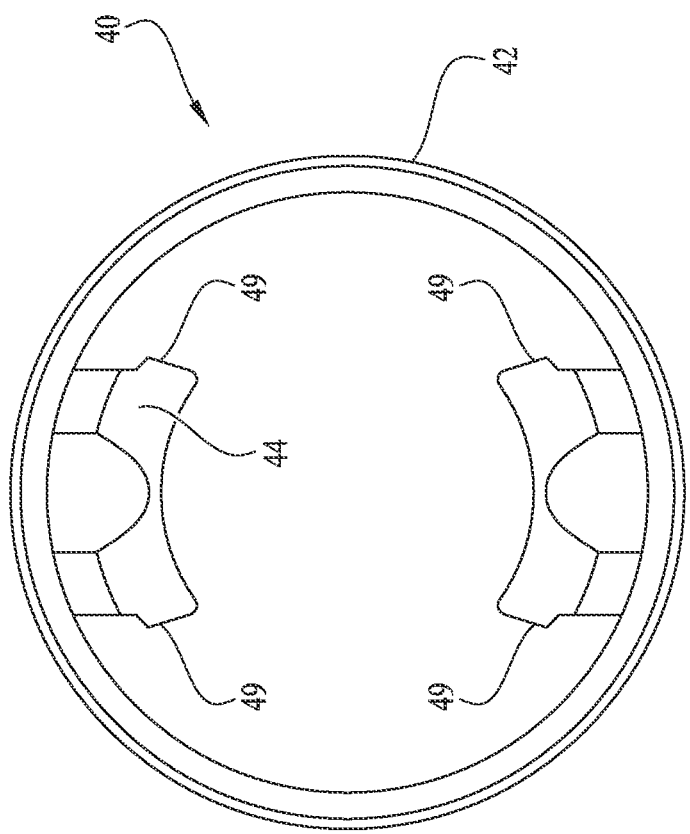
FIG. 7 is a top elevation view of a seal usable in the surgical tool of FIG. 1 according to another implementation.

In an implementation, the tabs 44 have a chamfered edge 48. The chamfered edge 48 helps a user insert the tabs through the outer hub holes 38. As shown in FIG. 7, the tabs 44 may have at least one angled barb 49 to prevent accidental removal of the tabs from the holes 38 in the outer hub 24. In an implementation, the angled barb 49 is configured to extend from about 0.01 inch to about 0.02 inch beyond the holes 38 in the outer hub.

In an implementation, the tool is configured so that the tabs 44 fit into the inner drive hub groove 36. Placement of the tabs 44 in the inner drive hub groove 36 prevents significant movement of the inner drive hub 14 in a proximal or distal direction relative to the outer driver hub 22.

Once the seal tabs 44 are inserted through the outer hub holes 38 and proximal to the inner drive hub boss 34, the tabs cooperate with the inner drive hub boss 34 to prevent the inner drive hub 14 from being removed from the outer hub 24 without either removing the seal from the assembly or through the use of excessive force. If the inner drive hub 14 is pulled outward from the proximal end of the outer hub 24, the boss 34 forces the tabs 44 to bend and to then become wedged between the boss and the outer hub. The boss 34 cannot move past the bent over tab 44 and this prevents the inner drive hub 14 from being withdrawn from the outer hub 24. The seal 40 may be made from materials that are flexible enough to allow the seal to be placed over the outer hub 24 and the tabs 44 positioned in the outer hub holes 38 and that have a limited amount of compression to prevent the boss 34 from moving past a bent over tab. In an implementation, the seal 40 is made of silicon rubber. Once the surgical tool 10 is coupled to the handpiece 12, the seal 40 provides a fluid tight seal with the walls of the handpiece 12.

The surgical tool may also have one or more magnets placed on the inner drive hub 14 and the outer hub 24 for tracking the position of the inner shaft 20 relative to the outer shaft 26, such as for controlling tool functionality. In an implementation, a cylindrical magnet 50 is mounted on the inner drive hub 14 and a cylindrical magnet 52 is mounted on the outer hub 24. An RFID tag may be placed on the surgical tool, such as for identification and usage tracking. In an implementation RFID tag 54 is wrapped around an outer surface of the outer hub 24. An RFID cover may be used to protect the RFID tag. In an implementation, an RFID cover 56 snaps into place around the outer hub 24 over the RFID tag 54.

A method of assembling a surgical tool according to an implementation will now be described. The inner drive hub 14 and the inner shaft 20 are inserted into the outer hub 24 and the outer shaft 26 until the boss 34 of the inner drive hub is positioned distally to the outer hub holes 38. The seal 40 is then placed over the outer hub 24 and the tabs inserted through the holes 38 in the outer hub 24 until the tabs extend into the groove 36 of the inner drive hub. In an implementation, RFID tag 54 is wrapped around an outer surface of the outer hub and RFID cover 56 is then snapped into place around the outer hub and RFID tag. In an implementation, prior to insertion of the inner drive hub 14 and shaft 20 into the outer hub 24 and outer shaft 26, magnet 50 is placed on the inner drive hub and magnet 52 is placed on the outer hub.

There is disclosed in the above description and the drawings, a surgical tool that fully and effectively overcomes the disadvantages associated with the prior art. However, it will be apparent that variations and modifications of the disclosed implementations may be made without departing from the principles of the invention. The presentation of the implementations herein is offered by way of example only and not limitation, with a true scope and spirit of the invention being indicated by the following claims.

Any element in a claim that does not explicitly state "means" for performing a specified function or "step" for performing a specified function, should not be interpreted as a "means" or "step" clause as specified in 35 U.S.C. § 112.

What is claimed is:

1. A surgical tool comprising:
   an inner drive hub coupled to an inner shaft, the inner drive hub further comprising a boss;
   an outer hub coupled to a hollow outer shaft, the outer drive hub further comprising at least one hole; and
   a seal comprising a body and at least one tab;
   wherein the inner drive hub and the inner shaft are configured for insertion inside the outer hub and the hollow outer shaft such that the boss is positioned distally to the at least one hole; and
   the seal body is positioned outside of the outer hub and the at least one tab extends through the at least one hole and proximally to the boss to removably couple the inner drive hub and the inner shaft to the outer hub and the hollow outer shaft;
   wherein the at least one tab cooperates with the inner drive hub to prevent the inner drive hub from being removed from the outer hub without removing the seal; and
   wherein if the inner drive hub is pulled outward from the outer hub, the boss forces the at least one tab to bend and become wedged between the boss and the outer hub, thereby preventing the boss from moving past the tab and preventing the inner drive hub from being withdrawn from the outer hub.

2. The surgical tool of claim 1 wherein the at least one hole is configured as a slot.

3. The surgical tool of claim 1 wherein the at least one tab has a chamfered edge.

4. The surgical tool of claim 1 wherein the at least one tab has a barb.

5. The surgical tool of claim 1 wherein the outer hub comprises a plurality of holes and the seal comprises a plurality of tabs; and wherein the seal is configured such that each of the plurality of tabs is inserted into a different one of the plurality of holes.

6. The surgical tool of claim 1 wherein the at least one tab has a rounded inner portion configured with a radius slightly larger than the radius of the inner drive hub.

7. The surgical tool of claim 1 wherein the seal is made of silicon rubber.

8. The surgical tool of claim 1 wherein the inner shaft is hollow and configured for connection to a drive hub with a suction device.

9. The surgical tool of claim 1 further comprising a first magnet coupled to the inner drive hub and a second magnet coupled to the outer hub.

10. The surgical tool of claim 1 further comprising an RFID tag coupled to the outer hub and an RFID cover coupled to outer hub over the RFID tag.

11. The surgical tool of claim 1 further comprising a blade coupled to a distal end of the inner shaft and a cutting head coupled to a distal end of the outer shaft.

12. The surgical tool of claim 1 wherein the at least one tab has a length and a thickness and wherein the length is greater than the thickness.

13. A surgical cutting tool comprising:
    an inner drive hub coupled to an inner shaft, the inner drive hub further comprising a groove;
    an outer hub coupled to a hollow outer shaft, the outer drive hub further comprising a plurality of slots; and
    a seal comprising a body and a plurality of tabs extending substantially perpendicularly from the body;
    wherein the inner drive hub and the inner shaft are configured for insertion inside the outer hub and the hollow outer shaft such that the groove is positioned proximally to the plurality of slots;
    the seal body is positioned outside of the outer hub;
    each of the plurality of tabs extends through a separate one of the plurality of slots and into the groove to removably couple the inner drive hub and the inner shaft to the outer hub and the hollow outer shaft;
    wherein the tabs cooperate with the inner drive hub to prevent the inner drive hub from being removed from the outer hub without removing the seal; and
    wherein if the inner drive hub is pulled outward from the outer hub, the tabs bend and become wedged between the inner hub and the outer hub, thereby preventing the inner drive hub from being withdrawn from outer hub.

14. The surgical cutting tool of claim 13 wherein the plurality of slots are positioned on opposite sides of the outer hub.

15. The surgical tool of claim 13 wherein the plurality of tabs each have a rounded inner portion configured with a radius slightly larger than the radius of the groove.

16. The surgical tool of claim 13 wherein each of the tabs has a chamfered edge.

17. The surgical tool of claim 13 wherein each of the tabs has at least one barb.

18. The surgical tool of claim 13 wherein the seal is made of silicon rubber.

19. The surgical tool of claim 13 wherein each of the plurality of tabs has a length and thickness and wherein the length is greater than the thickness.

* * * * *